(12) United States Patent
Mochly-Rosen et al.

(10) Patent No.: US 7,459,424 B2
(45) Date of Patent: *Dec. 2, 2008

(54) PEPTIDE INHIBITORS OF PROTEIN KINASE C γ FOR PAIN MANAGEMENT

(75) Inventors: Daria Mochly-Rosen, Menlo Park, CA (US); Sarah M. Sweitzer, Vallejo, CA (US); Joan J. Kendig, Campbell, CA (US); David C. Yeomans, Sunnyvale, CA (US)

(73) Assignee: The Borad of Trustees of the Leland Stanford Junior University, Stanford, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 10/421,548

(22) Filed: Apr. 22, 2003

(65) Prior Publication Data

US 2003/0223981 A1 Dec. 4, 2003

Related U.S. Application Data

(60) Provisional application No. 60/374,530, filed on Apr. 22, 2002.

(51) Int. Cl.
*A61K 38/00* (2006.01)
*C07K 7/00* (2006.01)

(52) U.S. Cl. .......................... 514/2; 530/300
(58) Field of Classification Search ............... None
See application file for complete search history.

(56) References Cited

U.S. PATENT DOCUMENTS

| 4,351,829 | A | 9/1982 | Zetler et al. |
| 5,776,685 | A | 7/1998 | Riedel |
| 5,783,405 | A | 7/1998 | Mochly-Rosen et al. |
| 5,935,803 | A | 8/1999 | Vasquez et al. |
| 6,165,977 | A | 12/2000 | Mochly-Rosen |
| 6,376,467 | B1 | 4/2002 | Messing et al. |
| 6,395,306 | B1 * | 5/2002 | Cui et al. ............ 424/539 |
| 2003/0223981 | A1 | 12/2003 | Mochly-Rosen |
| 2004/0009922 | A1 | 1/2004 | Mochly-Rosen |
| 2005/0215483 | A1 | 9/2005 | Mochly-Rosen |

FOREIGN PATENT DOCUMENTS

| WO | WO 94/04686 A1 | 3/1994 |
| WO | WO 97/14038 A1 | 4/1997 |
| WO | WO 99/43805 A1 | 9/1999 |
| WO | WO 00/01415 | 1/2000 |
| WO | WO 00/53218 | * 9/2000 |
| WO | WO 01/46252 A1 | 6/2001 |
| WO | WO 01/75067 | * 11/2001 |

OTHER PUBLICATIONS

Knopf, J. et al. Cell 46:491-502 (1986).*
Chen, L. et al. Chemistry & Biology 8: 1123-1129 (2001).*
Malmberg, A. et al. Science 278: 279-283 (1997).*
Jones et al., Cell Regulation 2: 1001-1009 (1991), "Molecular cloning of a second form of rac protein kinase".*
Meier et al., Journal of Biological Chemistry 272(48): 30491-30497 (1997), "Mitogenic activation, phosphorylation, and nuclear translocation of protein kinase B beta".*
Csukai et al., "Pharmacologic modulation of protein kinase C isozymes: the role of racks and subcellular localisation", Pharmacological Research 39(4): 253-259 (1999).*
Mochly-Rosen et al., "Anchoring proteins for protein kinase C: a means for isozyme selectivity", FASEB Journal 12: 35-42 (1998).*
Julius, D. and Basbaum, A.I., *Nature*, 413:203-210, (2001).
Igwe, O.J. and Chronwall, B.M., *Neuroscience* 104(3):875-890, (2001).
Martin, W.J., et al., *Neuroscience* 88(4):1267-1274, (1999).
Martin, W.J., et al., *The Journal of Neuroscience* 21(14):5321-5327, (2001).
Petersen-Zeitz, K.R. and Basbaum, A.I., *Pain Supplement* 6:S5-S12, (1999).
Wen, Z.H., et al., *Neuroscience Letters* 309:25-28, (2001).
Stebbins, E.G. and Mochly-Rosen, D., *The Journal of Biological Chemistry*, 276(32):29644-29650, (2001).
Chen, L., et al., *PNAS*, 98(20):11114-11119, (2001).
Falnes, P.O., et al., *Biochemistry* 40:4349-4358, (2001).
Aley et al., *The Journal of Neurosceince*, 20(12):4680-4685 (2000).
Dina et al., *The Journal of Neurosceince*, 20(22):8614-8619 (2000).
Ono et al., *Science*, 236:1116-1120 (1987).
Kubo et al., *FEBS Letters*, 223(1):138-142 (1987).
Gokmen-Polar et al., "Mapping of a Molecular determinant for Protien Kinase C Betall Isozyme Function", *The Journal of Biological Chemistry*, 273(32):20261-20266 (1998).
Sweitzer et al., "Developmental Regulation of Inflammatory Pain by Protein Kinase C", Society for Neuroscience Abstract Viewer and Itinerary Planner, 32nd Annual Meeting of the Society of Neuroscience (2002).

* cited by examiner

*Primary Examiner*—Anand U Desai
(74) *Attorney, Agent, or Firm*—Judy M. Mohr; King & Spalding LLP

(57) ABSTRACT

Peptide sequences derived from the V5 domain of isozymes of protein kinase C for use in pain management are described. Also described are compositions comprising the peptides for treating pain and/or inducing analgesia. Methods of pain treatment and methods of identifying compounds that mimic the activity of the peptides are also described.

8 Claims, 6 Drawing Sheets

```
              1         5            10                      25                      35
γPKC   PRPCGRSG ENFDKFFTRA APALTPPDRL VLASIDQADF QGFTYVNPDF VHPDARSPTS PVPVPVM   (SEQ ID NO:1)
              (SEQ ID NO:3)           (SEQ ID NO:4)

1      5       10
ε-PKC  PRIK TKRDVNNFDQ DFTREEPVLT LVDEAIVKQI NQEEFKGFSY FGEDLMP   (SEQ ID NO:2)
              (SEQ ID NO:5)
```

Fig. 1

PEPTIDE INHIBITORS OF PROTEIN KINASE C γ FOR PAIN MANAGEMENT

This application claims the benefit of U.S. provisional application No. Ser. 60/374,530, filed Apr. 22, 2002, which is incorporated herein by reference.

This work was supported in part by The National Institutes of Health grant numbers NS13108 and DA08256. Accordingly the United States government may have certain rights in this invention.

FIELD OF THE INVENTION

The present invention relates to peptides having specific inhibitory activity for the gamma isozyme of protein kinase C and/or for the epsilon isozyme of protein kinase C, and their use for the management and/or lessening of pain. More particularly, the invention relates to compositions comprising peptides from the variable (V5) region of PKCγ and PKCε isozymes for use as therapeutic agents in the management of pain.

BACKGROUND OF THE INVENTION

More than 75 million people in the U.S. suffer from chronic disabling pain (NIH Guide, 1998). Chronic pain in America is a large social and economic burden, with costs exceeding $50 billion annually in lost wages, lost productivity, medical expenses, and the like. Additional costs are more difficult to quantify, such as the physical and emotional impacts on a pain sufferer and their family members.

Normal pain is an important self-protection mechanism employed by the body. Upon the occurrence of harmful stimulus, the peripheral nociceptors (pain-sensing primary afferent neurons) detect and send the signal of pain through Aβ, Aδ, and C fibers to the dorsal horn of the spinal cord. The dorsal horn processes the incoming signals, and upon accumulation of signals, transmits the information to supraspinal sites that in turn dictate a response, for example, withdrawal of a foot from heat. In a normal, physiological pain response, the pain sensation resolves upon cessation of the harmful stimulus.

Chronic pain, unlike normal pain, does not abate. A number of physiological changes in the spinal cord, dorsal root ganglia (DRG), and the brain have been observed, which correspond to the state of chronic pain. The exact mechanism of the evolution of chronic pain has not been elucidated; however, central sensitization has been shown to play a role in the onset of chronic pain. C fibers are likely to be dominantly activated in most cases of chronic pain based on evidence that these fibers are predominately activated in tests employing a low rate of heating, while high-rate heating activates Aδ fibers.

Chronic neuropathic pain results from aberrant sensory processing in either the peripheral and/or the central nervous system (CNS), typically caused by an initial inflammatory, immunological, or viral episode, or by ischemic or mechanical insult to a nerve. Neuropathic pain is characterized by an altered pain perception that can manifest as allodynia, a response to a normally non-noxious stimulus (e.g., the touch of clothing becomes painful), or as hyperalgesia, a decreased threshold to noxious stimuli (e.g., warm water on burned skin).

Traditional pharmacological therapies and surgical intervention are ineffective in treating many types of pain. Therapies that do exist, such as opioids, are often ineffective in the long-term due to the development of tolerance and side effects. Therefore, there remains a great need for new, highly specific agents which, when used alone or in conjunction with existing therapies, would alleviate suffering from pain.

Protein kinase C (PKC) is a key enzyme in signal transduction involved in a variety of cellular functions, including cell growth, regulation of gene expression, and ion channel activity. The PKC family of isozymes includes at least 11 different protein kinases which can be divided into at least three subfamilies based on their homology and sensitivity to activators.

Members of the classical or cPKC subfamily, $\alpha$, $\beta_I$, $\beta_{II}$ and $\gamma$PKC, contain four homologous domains (C1, C2, C3 and C4) inter-spaced with isozyme-unique (variable or V) regions, and require calcium, phosphatidylserine (PS), and diacylglycerol (DG) or phorbol esters for activation. The classical PKC family, $\alpha$, $\beta_I$, $\beta_{II}$, and $\gamma$ isozymes are found in the superficial laminae of the dorsal horn in the spinal cord.

Members of the novel or nPKC subfamily, $\delta,\epsilon,\eta$, and $\theta$PKC, lack the C2 homologous domain and do not require calcium for activation. $\epsilon$PKC is found in primary afferent neurons both in the dorsal root ganglia (DRG) as well as in the superficial layers of the dorsal spinal cord.

Finally, members of the atypical or aPKC subfamily, $\zeta$ and $\lambda/\iota$PKC, lack both the C2 and one half of the C1 homologous domains and are insensitive to DG, phorbol esters, and calcium.

Studies on the subcellular distribution of PKC isozymes demonstrate that activation of PKC results in its redistribution in the cells (also termed translocation), such that activated PKC isozymes associate with the plasma membrane, cytoskeletal elements, nuclei, and other subcellular compartments (Saito, N. et al., *Proc. Natl. Acad. Sci. USA* 86:3409-3413 (1989); Papadopoulos, V. and Hall, P. F. *J. Cell Biol.* 108:553-567 (1989); Mochly-Rosen, D., et al., *Molec. Biol. Cell* (formerly *Cell Reg.*) 1:693-706, (1990)).

The unique cellular functions of different PKC isozymes are determined by their subcellular location. For example, activated $\beta_I$PKC is found inside the nucleus, whereas activated $\beta_{II}$PKC is found at the perinucleus and cell periphery of cardiac myocytes (Disatnik, M. H., et al., *Exp. Cell Res.* 210:287-297 (1994)). The localization of different PKC isozymes to different areas of the cell in turn appears due to binding of the activated isozymes to specific anchoring molecules termed Receptors for Activated C-Kinase (RACKs). RACKs are thought to function by selectively anchoring activated PKC isozymes to their respective subcellular sites. RACKs bind only fully activated PKC and are not necessarily substrates of the enzyme. Nor is the binding to RACKs mediated via the catalytic domain of the kinase (Mochly-Rosen, D., et al., *Proc. Natl. Acad. Sci. USA* 88:3997-4000 (1991)). Translocation of a PKC reflects binding of the activated enzyme to RACKs anchored to the cell particulate fraction and the binding to RACKs is required for a PKC to produce its cellular responses (Mochly-Rosen, D., et al., *Science* 268: 247-251 (1995)). Inhibition of PKC binding to RACKs in vivo inhibits PKC translocation and PKC-mediated function (Johnson, J. A., et al., *J. Biol. Chem* 271:24962-24966 (1996a); Ron, D., et al., *Proc. Natl. Acad. Sci. USA* 92:492-496 (1995); Smith, B. L. and Mochly-Rosen, D., *Biochem. Biophys. Res. Commun.* 188:1235-1240 (1992)).

In general, translocation of PKC is required for proper function of PKC isozymes. Peptides that mimic either the PKC-binding site on RACKs (Mochly-Rosen, D., et al., *J. Biol. Chem.*, 226:1466-1468 (1991a); Mochly-Rosen, D., et al., supra, 1995) or the RACK binding site on PKC (Ron, et al., supra, 1995; Johnson, J. A. et al., supra, 1996a) are isozyme-specific translocation inhibitors of PKC that selectively inhibit the function of the enzyme in vivo.

Three PKC isozymes have been shown to participate in the sensation of pain (the nociception pathway): βII, γ, and ε (Igwe O. J., et al., *Neuroscience* 104(3):875-890 (2001); Martin W. J., et al., *Neuroscience* 88(4):1267-1274 (1999) Khasar S. G., et al., *Neuron* 24(1):253-60 (1999)). βIIPKC was found to be activated in hyperalgesia induced by peripheral inflammation with complete Freund's adjuvant (Igwe O. J., et al., *Neuroscience* 104(3):875-890 (2001)). Another study suggested that γPKC was activated upon injury with the same agent (Martin W. J., et al., *J. Neuroscience* 21(14):5321-5327 (2001)), and that γPKC deficient mice show greatly reduced hyperalgesia following an inflammatory nerve injury (Martin W. J., et al., *Neuroscience* 88(4):1267-1274 (1999)). εPKC deficient mice exhibit attenuated hyperalgesic responses to thermal stimulation following inflammation, suggesting that εPKC also plays an important role in nociceptor function (Khasar S. G., et al., *Neuron* 24(1):253-60 (1999)). Use of non-specific PKC inhibitors like calphostin in a neuropathy model (Ohsawa M., et al., *Eur. J. Pharmacol.,* 372(3):221-8 (1999)), NPC15437 in a capsaicin model (Sluka K. A., et al., *Pain,* 71(2):165-178 (1997)), and chelerythrine in a formalin model (Hua X. Y., et al., *Neurosci Lett.,* 276(2):99-102 (1999)) all showed reversal of the allodynia and/or hyperalgesia induced by the inflammatory agents.

The role of εPKC in pain perception has also been described (WO 00/01415; U.S. Pat. No. 6,376,467), and the εV1-2 peptide, a selective inhibitor of εPKC, was reported to lessen pain.

Despite such findings that PKC in general appears to play a role in nociception, few peptide sequences involved in nociception have been identified. To date, only a handful of εPKC V1 peptides have been described as therapeutically effective for the management of pain. The present invention is concerned with providing additional PKC isozyme targets and PKC isozyme/region specific peptides for the development of non-opioid based pain treatments.

SUMMARY OF THE INVENTION

Accordingly, it is an object of the invention to provide a PKC peptide having specific activity for one or more PKC isozymes for pain management.

It is a further object of the invention to provide a PKC peptide derived from the V5 region of a PKC isozyme that has specific activity for that isozyme in nociception.

It is yet another object of the invention to provide compositions and methods using peptides derived from the V5 region of PKCγ and PKCε for management of pain.

Accordingly, in one aspect, the invention includes a peptide derived from the V5 domain of gamma- protein kinase C (γPKC) or epsilon protein kinase C (εPCK), where the peptide has isozyme-specific activity for modulation of pain.

In one embodiment, the peptide's isozyme-specific activity is an inhibitory activity that attenuates nociception.

In another embodiment, the peptide has a sequence that corresponds to a sequence of amino acids determined from the first 10 residues of the V5 domain. In yet another embodiment, the peptide has a sequence that corresponds to a sequence of amino acids determined from residues between the 25th and 35th residues of the V5 domain, inclusive.

An exemplary sequence that corresponds to a sequence of amino acids derived from residues between the 25th and 35th amino acid residues of the V5 domain of γPKC is SEQ ID NO:4. Exemplary sequences derived from the residues within the first 10 residues of the V5 domain of γPKC and εPCK are, respectively, SEQ ID NO:3 and SEQ ID NO:5.

The peptide, in one embodiment, is formulated for transport across a cell membrane. For example, the peptide is conjugated to a carrier peptide or is formulated in a delivery vehicle capable of membrane transport.

In another aspect, the invention includes a method of lessening pain, comprising administering a peptide (i) derived from the V5 domain of γPKC or εPCK and (ii) having isozyme-specific activity.

In one embodiment, the method includes a step of, prior to administering the peptide, determining whether a selected V5 domain peptide has specific activity for γPKC or εPCK. In vitro and in vivo methods of determine isozyme specific activity are described herein and are known in the art. In this embodiment, management of pain is achieved by determining whether a selected V5 domain peptide has isozyme-specific activity for γPKC and/or εPCK; and if the peptide has such activity, providing the peptide for administration to a subject in need of pain management.

In another embodiment, the method includes administering or providing for administration a peptide selected from the sequences identified herein as SEQ ID NO:3, SEQ ID NO:4, and SEQ ID NO:5.

The peptides can be administered via injection or via local delivery to a site of pain. In one embodiment, local delivery is achieved by topical, intradermal, or transdermal application.

The method of the invention is contemplated for treatment of acute pain or chronic pain, as well as for prophylactic treatment of anticipated pain.

In yet another aspect, the invention includes a method of identifying a compound that modulates pain. The method includes measuring the activity of a peptide selected from the group consisting of SEQ ID NO:3, SEQ ID NO:4, and SEQ ID NO:5 in the presence and absence of a test compound; and selecting the test compound as being effective to modulate pain if the activity of the peptide is altered in the presence of the test compound.

Measuring the activity of the peptide, in one embodiment, is achieved by conducting a competitive binding assay in the presence of the test compound.

Selection of the test compound as being effective for management of pain, in one embodiment, is made if binding of the peptide is decreased in the presence of the test compound.

An exemplary test compound, in one embodiment, is an organic compound.

An additional aspect includes the use of the peptide inhibitors in the preparation of a medicament for use in the treatment of pain.

These and other objects and features of the invention will be more fully appreciated when the following detailed description of the invention is read in conjunction with the accompanying drawings.

BRIEF DESCRIPTION OF THE DRAWINGS

FIG. 1 shows the sequences of the V5 domains of PKCγ and PKCε, with peptides derived from the V5 domain for use in pain management indicated in bold.

BRIEF DESCRIPTION OF THE SEQUENCES

Figure 2A:
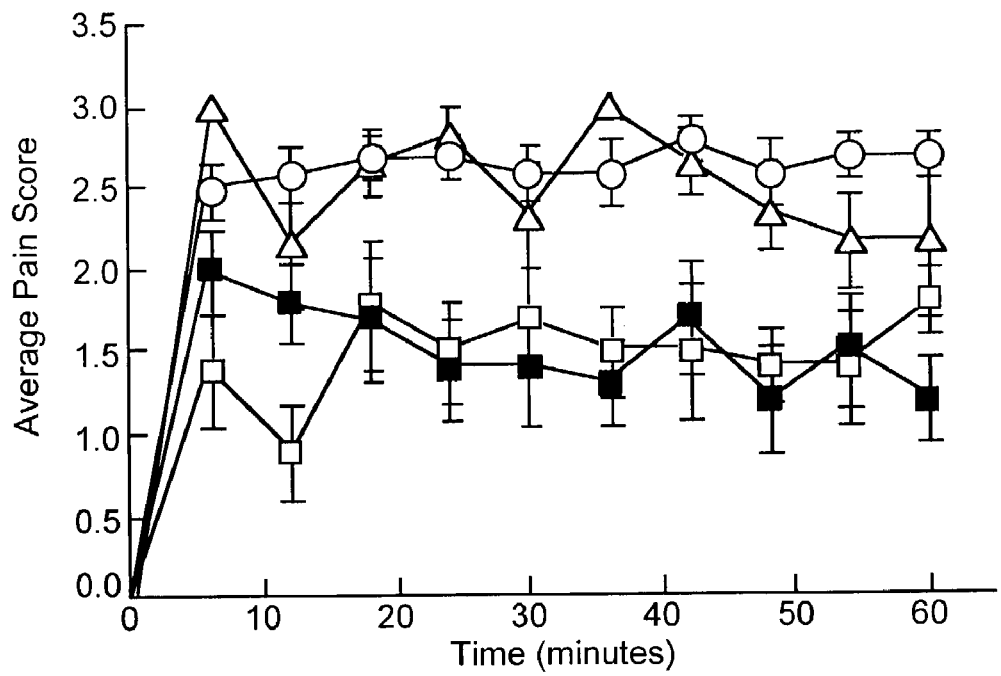
FIGS. 2A-2C are plots showing the pain score as a function of time, in minutes, for rat pups at postnatal days 7 (FIG. 2A), 15 (FIG. 2B), and 21 (FIG. 2C) treated with a γPKC peptide derived from the V5 domain (closed squares), a V1 domain εPCK peptide as a positive control (open squares), a carrier peptide (open triangle), or saline (open circle), followed by intradermal administration of formalin to the paw.

SEQ ID NO: 1 corresponds to a peptide from the V5 domain of γPKC.
SEQ ID NO:2 corresponds to a peptide from the V5 domain of εPKC.
SEQ ID NO:3 is a peptide derived from the V5 domain of the y isozyme of PKC.
SEQ ID NO:4 is a peptide derived from the V5 domain of the γ isozyme of PKC.
SEQ ID NO:5 is a peptide derived from the V5 domain of the ε isozyme of PKC.
SEQ ID NO:6 is a peptide derived from the V1 domain of εPKC.
SEQ ID NO:7 is a Tat-derived carrier peptide (Tat 47-57).
SEQ ID NO:8 is the *Drosophila Antennapedia* homeodomain-derived carrier peptide.
SEQ ID NO:9 is a modification of SEQ ID NO:4.
SEQ ID NO:10 is a modification of SEQ ID NO:4.
SEQ ID NO:11 is a modification of SEQ ID NO:4.
SEQ ID NO:12 is a modification of SEQ ID NO:4.
SEQ ID NO:13 is a modification of SEQ ID NO:4.
SEQ ID NO:14 is a modification of SEQ ID NO:4.
SEQ ID NO:15 is a modification of SEQ ID NO:4.
SEQ ID NO:16 is a modification of SEQ ID NO:4.
SEQ ID NO:17 is a modification of SEQ ID NO:4.
SEQ ID NO:18 is a modification of SEQ ID NO:4.
SEQ ID NO:19 is a modification of SEQ ID NO:4.

DETAILED DESCRIPTION OF THE INVENTION

I. Definitions

Unless otherwise indicated, all terms herein have the same meaning as they would to one skilled in the art of the present invention. Practitioners are particularly directed to *Current Protocols in Molecular Biology* (Ausubel, F. M. et al., John Wiley and Sons, Inc., Media Pa.) for definitions and terms of the art.

Abbreviations for amino acid residues are the standard 3-letter and/or 1-letter codes used in the art to refer to one of the 20 common L-amino acids.

A "conserved set" of amino acids refers to a contiguous sequence of amino acids that is conserved between members of a group of proteins. A conserved set may be anywhere from two to over 50 amino acid residues in length. Typically, a conserved set is between two and ten contiguous residues in length. For example, for the two peptides RLVLAS (SEQ ID NO:4) and KLVLAS (SEQ ID NO:9), there are 5 identical positions (LVLAS) which form the conserved set of amino acids for these two sequences.

"Conservative amino acid substitutions" are substitutions which do not result in a significant change in the activity or tertiary structure of a selected polypeptide or protein. Such substitutions typically involve replacing a selected amino acid residue with a different residue having similar physicochemical properties. For example, substitution of Glu for Asp is considered a conservative substitution since both are similarly-sized negatively-charged amino acids. Groupings of amino acids by physico-chemical properties are known to those of skill in the art.

"Peptide" and "polypeptide" are used interchangeably herein and refer to a compound made up of a chain of amino acid residues linked by peptide bonds. Unless otherwise indicated, the sequence for peptides is given in the order from the amino terminus to the carboxyl terminus.

Two amino acid sequences or two nucleotide sequences are considered homologous (as this term is preferably used in this specification) if they have an alignment score of >5 (in standard deviation units) using the program ALIGN with the mutation gap matrix and a gap penalty of 6 or greater (Dayhoff, M. O., in ATLAS OF PROTEIN SEQUENCE AND STRUCTURE (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, more preferably 70%, still more preferably 80%, identical when optimally aligned using the ALIGN program mentioned above.

A peptide or peptide fragment is "derived from" a parent peptide or polypeptide if it has an amino acid sequence that is identical or homologous to at least a contiguous sequence of five amino acid residues of the parent peptide or polypeptide.

The terms "induce analgesia", "induction of analgesia" and the like refer to the ability of a peptide to manage pain, typically to attenuate pain, as evidenced by favorable results in one or more conventional laboratory models for testing pain or assessing analgesia, such as the tests described herein, such as the formalin model and the capsaicin model. Suitable models for determining induction of analgesia in human subjects are known and include, for example, those indicated in the subsequent paragraph.

"Lessening pain" refers to a process by which the level of pain a subject perceives is reduced relative to the level of pain the same or a similar subject perceived (or would have perceived) in the absence of or prior to the administration of a therapeutic agent. Pain levels can be calibrated on a subjective scale, or by measuring the subject's response to the pain by, for example, release of stress related factors or the activity of pain-transducing nerves in the peripheral nervous system or the central nervous system. Pain levels can also be calibrated by measuring the amount of an analgesic required for the subject to report that no pain is present or for a subject to stop exhibiting symptoms of pain.

"Modulate pain" intends a lessening, an increase, or some other measurable change in a level of pain.

"Pain management" intends both a lessening of pain and/or induction of analgesia.

A peptide has "specific activity" when it acts on a particular PKC isozyme involved in the nociception pathway, as opposed to non-specific peptides or compounds that fail to discriminate between PKC isozymes.

The term "treatment" or "treating" means any treatment of pain in a mammal, including: (a) preventing or protecting against nociception, that is, causing the clinical symptoms not to develop; (b) inhibiting nociception, that is, arresting or suppressing the development of clinical symptoms; and/or (c) relieving nociception, that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis." The term "effective amount" means a dosage sufficient to provide treatment for the disorder or disease state being treated. This will vary depending on the patient, the disease, and the treatment being effected.

II. Peptides for Pain Management

In one aspect, the invention provides peptides capable of selective inhibition of a particular PKC isozyme for the management of pain. As will be described below, these peptides are administered as therapeutic agents for use in modulating pain, typically for use in lessening pain, preventing future pain, and/or inhibiting heightened sensitivity to noxious stimuli. The ability of the peptides to selectively perform these activities, via selective inhibition of a single selected isozyme of PKC, reduces unwanted side effects.

The peptides described herein are derived from a variable domain of each PKC isozyme, the V5 domain. More specifically, the peptides correspond to peptide fragments from the V5 domain of γPKC and of εPKC. FIG. 1 shows the sequences of the V5 domain of γPKC and of εPKC, SEQ ID NO:1 and SEQ ID NO:2, respectively. The γPKC V5 domain corresponds to amino acid residues 633 et seq. of the peptide. The εPKC V5 domain corresponds to amino acid resides 687 et seq. of the peptide.

FIG. 1 also shows two peptide fragments derived from the V5 region of γPKC, indicated in bold in the figure and identified herein as SEQ ID NO:3 and SEQ ID NO:4. A peptide fragment derived from the V5 domain of εPKC is also indicated in bold in FIG. 1 and identified as SEQ ID NO: 5. In one embodiment, the peptide corresponds to a peptide derived from the first 10 residues of the V5 region of the parent isozyme. FIG. 1 numerically identifies residues 1, 5, 10, 25, and 35 of the V5 domains of the shown isozymes. SEQ ID NO:3 and SEQ ID NO:5 are peptides which correspond to contiguous residues in the first ten residues of the V5 domain of the isozyme. In another embodiment, the peptide corresponds to residues determined from a contiguous sequence of residues within positions 25-35, inclusive, of the V5 domain of the isozyme. SEQ ID NO:4 is exemplary for the γPKC isozyme. The peptides of the present invention include the above-described fragments as well as modifications thereof, particularly where the modifications entail conservative amino acid substitutions, and exemplary modifications are given below.

In studies performed in support of the invention, the γPKC peptide identified as SEQ ID NO:4 was used as an exemplary γPKC antagonist peptide to modulate nociception. Two pain models were used where acute inflammatory pain was induced by capsaicin or by formalin. These capsaicin-based and formalin-based models have long-term increases of sensitivity to noxious stimuli and are useful in modeling human pathological pain.

The capsaicin model of inflammation, together with a low rate thermal test, mimics central sensitization and hyperalgesia resulting from chronic pain. Application of capsaicin to the skin produces a robust, hours-long, C fiber selective hyperalgesia indicated by significant lowering of paw withdrawal latencies during low heating rate thermal tests. Capsaicin is the active ingredient in spicy "hot" foods. The receptor for capsaicin, VR-1 vanilloid receptor found on C fibers, has been recently cloned. It is a ligand-gated, non-selective cation channel. In addition to responding to capsaicin, VR-1 also responds to thermal stimuli (approximately 43° C.) (Kidd B. L., et al., *Br. J. Anaesth.*, 87(1):3-11 (2001)) and to protons, suggesting that its activity is enhanced during inflammation. Capsaicin has been shown to selectively activate and sensitize C fibers, and not Aδ. Therefore, Aδ latency measurements were used as controls for animal wellbeing during the studies.

The formalin model in rodents has been validated as a predictive test of treating injury-induced pain in humans (Dennis, S. G. and Meizack, R. in Advances in Pain Research and Therapy, Vol. 3,747, Eds. J. J. Bonica et al., Raven Press New York, 1979; Tjolsen, A., et al., *Pain,* 51:5-17 (1992)). The model produces a bi-phasic response, where the initial phase is triggered by a primary afferent barrage, similar in character to that described for the acute phasic tests except that chemical nociceptors are the mediators. The second phase is considered to be the hyperalgesic spontaneous activity that results from the initial tissue damage and reflects the lowering of nociceptive threshold plus the priming or "wind up" of the corresponding spinal circuitry. Thus, both peripheral and central neuronal circuits and mediators are required to induce and sustain this painful tissue-injury condition.

Example 1 describes a study where the ability of a PKCγ inhibitor peptide (SEQ ID NO:4) to modulate pain in rat pups was investigated. The rat provides an excellent model to study pain processing since the development of the rat nervous system at postnatal day 7 corresponds to that of a full term human infant, and at postnatal day 21 rats model a human preschool age child (Fitzgerald and Anand, Pain Management in Infants, Children and Adolescents (Schetchter et al., Eds.), pp 11-32. Baltimore, Md., Williams and Williams, 1993). In addition to developmental similarities, both rats and humans exhibit hypersensitivity in response to repeated stimulation that declines with age (Fitzgerald et al., *Developmental Medicine and Child Neurology,* 30:520 (1988); Fitzgerald et al., *Proceedings National Academy of Science USA,* 96:7719 (1999)).

In the study detailed in Example 1, the peptide identified herein as SEQ ID NO:4 was administered to rat pups on postnatal days 7, 15, and 21. The peptide was administered 15 minutes prior to intraplantar formalin injection. Following formalin injection, spontaneous pain behaviors were recorded every two minutes for one hour. In this study, an εPKC antagonist peptide from the V1 domain was used as a positive, comparative control. As noted above, the εV1-2 peptide, EVASLKPT (SEQ ID NO:6) has been described, for example, in U.S. Pat. No. 5,783,405 and by Dorn et al. (*PNAS,* 46(22):12798 (1999)). The εV1-2 peptide has been shown to selectively inhibit PCKε action and ameliorate pain (WO 00/01415).

Both the εV1-2 peptide and the γPKC peptide V5-3 (SEQ ID NO:4) were conjugated via terminal cysteine residues to a carrier peptide, Tat (SEQ ID NO:7), for administration. One group of animals was treated with the Tat carrier peptide alone as a control. Another group of animals received only saline as a control.

Figure 2B:
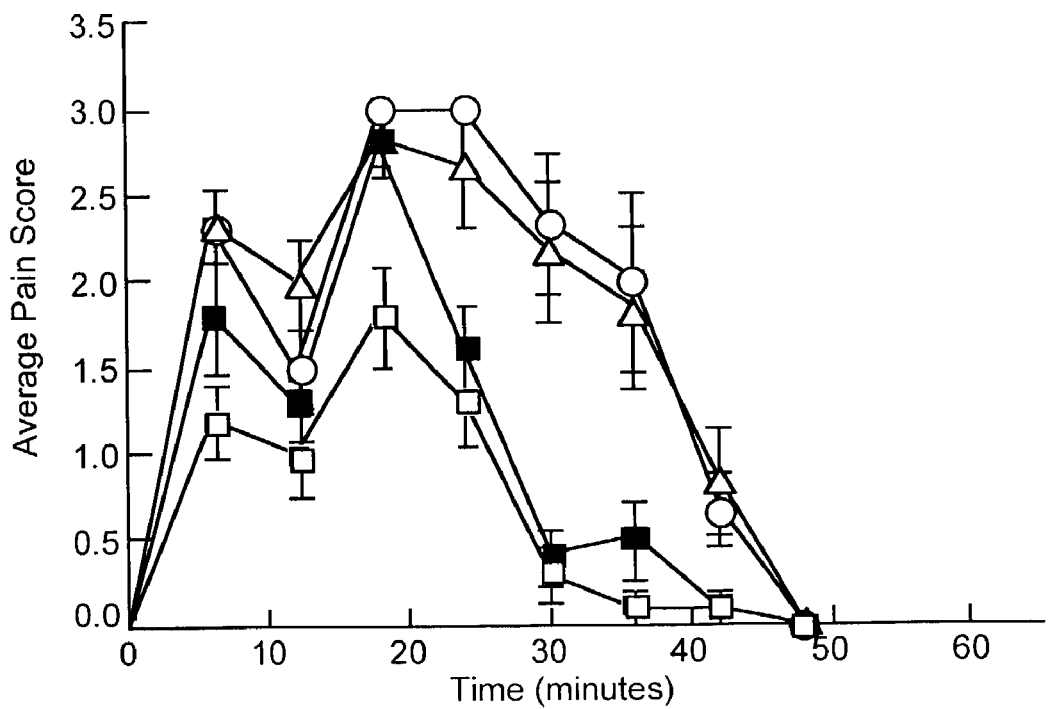
Figure 2C:
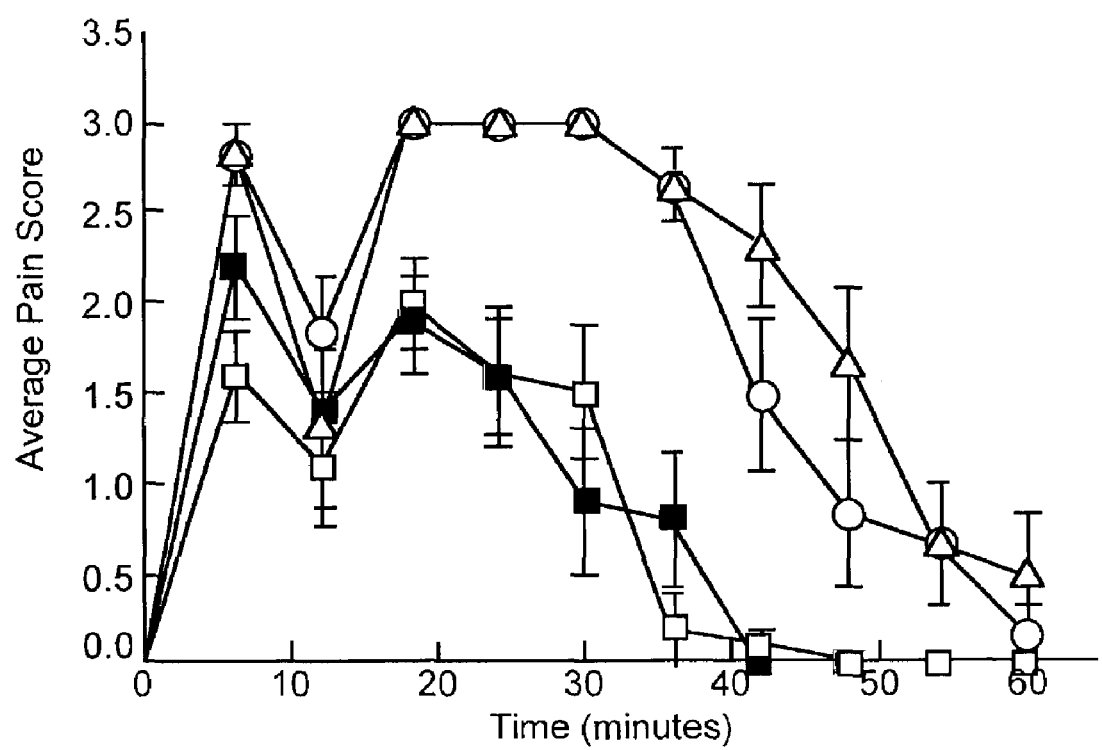

The results are shown in FIGS. 2A-2C, where average pain scores for rat pups treated with γPKC (closed squares), εPCK (open squares), the Tat carrier peptide alone (open triangles), or saline (open circles) are shown as a function of time, in minutes. The average pain score was determined by a time sampling method, where the animal's behavior was recorded every two minutes. A score of "1" was given if the animal was licking, shaking, or elevating the formalin-treated paw. The three pain scores over a six minute period of observation were summed into a single score, to give a maximum possible score of 3 for each animal for each six minute interval. The average pain score was determined from the individual scores of the animals in each treatment group. FIG. 2A corresponds to the average pain scores for 7 day old rat pups, where 1% formalin was administered to the paw 15 minutes post delivery of the peptide or control substance. The data in FIG. 2A shows that the γPKC peptide (SEQ ID NO:4) was effective to lessen pain, as evidenced by the decreased pain score relative to the control pups.

FIG. 2B shows the data for 15 day old rat pups, where 2.5% formalin was administered 15 minutes delivery of the test or control substances. The γPKC peptide was effective to alleviate pain, as evidenced by a decreased pain score relative to the control pups.

FIG. 2C shows the pain scores for 21 day old rat pups, where 2.5% formalin was administered 15 minutes after the test or control substances. The γPKC peptide provided a reduction in pain, as evidenced by the decreased pain score relative to the control pups.

In summary, the data in FIGS. 2A-2C show that γPKC peptide inhibitor attenuated formalin-induced spontaneous pain behaviors. Additionally, the γPKC peptide effectively shortened the duration of formalin-induced pain. It is noted that the εPKC V1 peptide provided a greater attenuation of formalin-induced nociception in postnatal day 7 pups (FIG. 2A), whereas both isozymes contribute to nociception relief on postnatal days 15 and 21. This suggests a strategy for treating neo-natal and/or pediatric pain by appropriate selection of a PKC isozyme in accord with developmentally specific patterns of nociception.

Example 2 describes another study in support of the invention, where a γPKC V5 domain peptide (SEQ ID NO:4) was used for pain management in the capsaicin pain model. As a positive, comparative control, a V1 εPKC peptide (SEQ ID NO:6) was used. The peptides were conjugated to a Tat carrier peptide (SEQ ID NO:7) and were administered intrathecally to test animals prior to application of capsaicin to a paw. Thirty minutes after capsaicin application, paw withdrawal latency was measured at regular intervals for 75 minutes. The results are shown in FIG. 3, for Tat-derived γPCK (closed squares), Tat-derived-εPCK (open squares), the Tat carrier peptide alone (open triangles), and for animals treated with saline (open circles).

Figure 3:
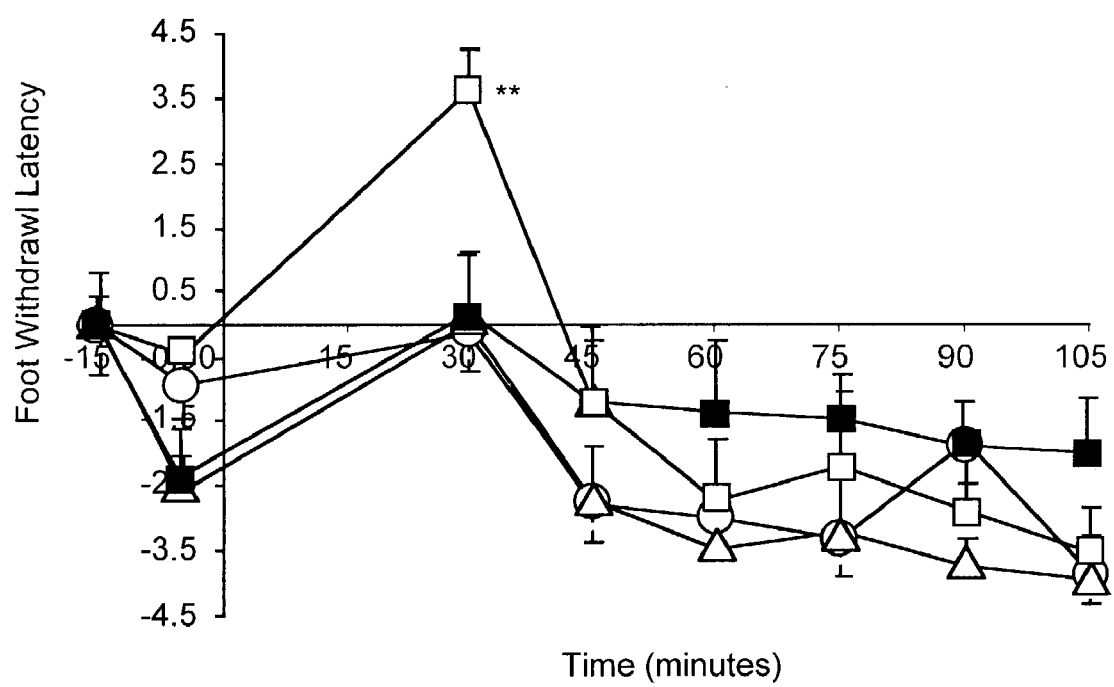
FIG. 3 is a plot showing the paw withdrawal latency as a function of time, using the capsaicin-induced nociception model in rats following intrathecal injection with a V5 domain γPKC peptide (closed squares) a V1 domain εPKC peptide as a positive control (open squares), a carrier peptide alone (open triangles), and saline (open circles).

FIG. 3 shows that the γPKC V5 domain peptide was effective to modulate the response to nociception. Specifically, the γPKC antagonist (SEQ ID NO:4) induced an analgesic effect, producing an increase of threshold in the initial time point. The dip at −5 minutes is likely due to the insult of intrathecal injection. The εPKC V1 antagonist was anti-hyperalgesic, reducing the paw withdrawal latency by about 50%.

In postnatal day 21 and older rats, intraplantar formalin produces a stereotypic biphasic behavioral pattern. Phase 1 is characterized by intense shaking, lifting and licking of the offending hindpaw produced by activation of peripheral nociceptors. Activation of descending inhibitory pathways follows, reducing spontaneous pain behaviors (quiescent phase). Quiescence is followed by a second phase, characterized by a revival of pain behaviors, and at least partially mediated by central mechanisms. Rats at postnatal day 15 exhibit a primitive biphasic response of shorter duration than observed in rats at postnatal day 21 and older. In contrast, rats at postnatal day 7 are 4-fold more sensitive to the nociceptive effects of intraplantar formalin compared to adult rats and exhibit a monophasic response pattern (Guy et al., supra (1992); Teng et al., supra (1998)).

Figure 4A:
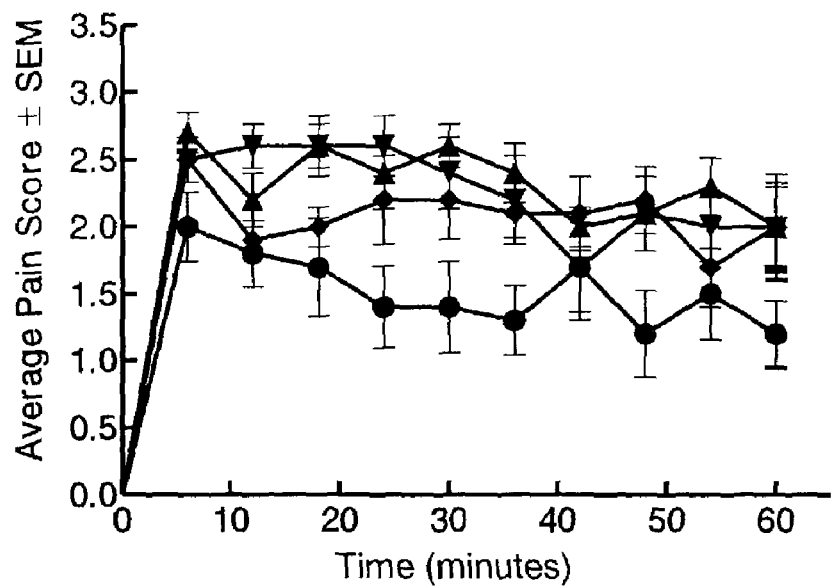
FIGS. 4A-4C are plots showing the average pain score as a function of time, in minutes, using the formalin-induced pain model in rats at postnatal day 7 (FIG. 4A), postnatal day 15 (FIG. 4B) and postnatal day 21 (FIG. 4C) following administration of 2 μM γPKC (inverted triangles), 10 μM γPKC (diamonds), or 20 μM γPKC (circles), or 10 μM of a carrier peptide control (triangles).
Figure 4B:
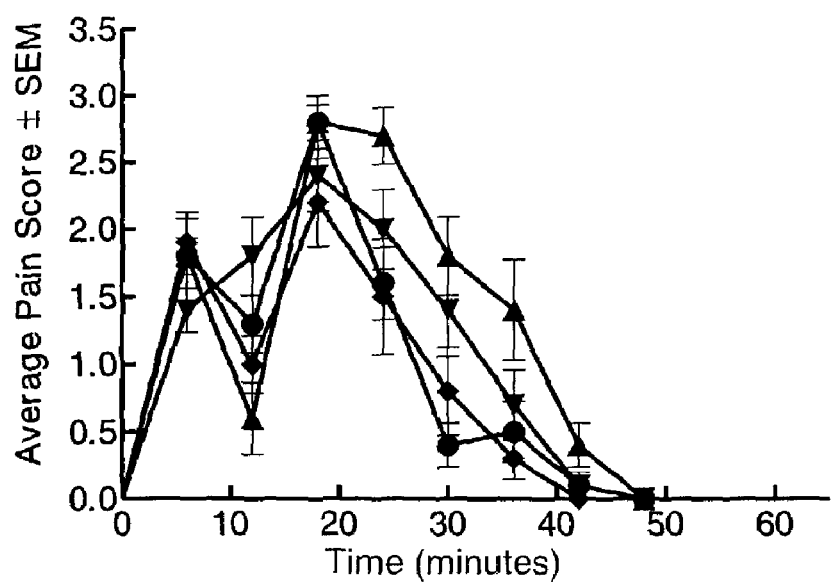
Figure 4C:
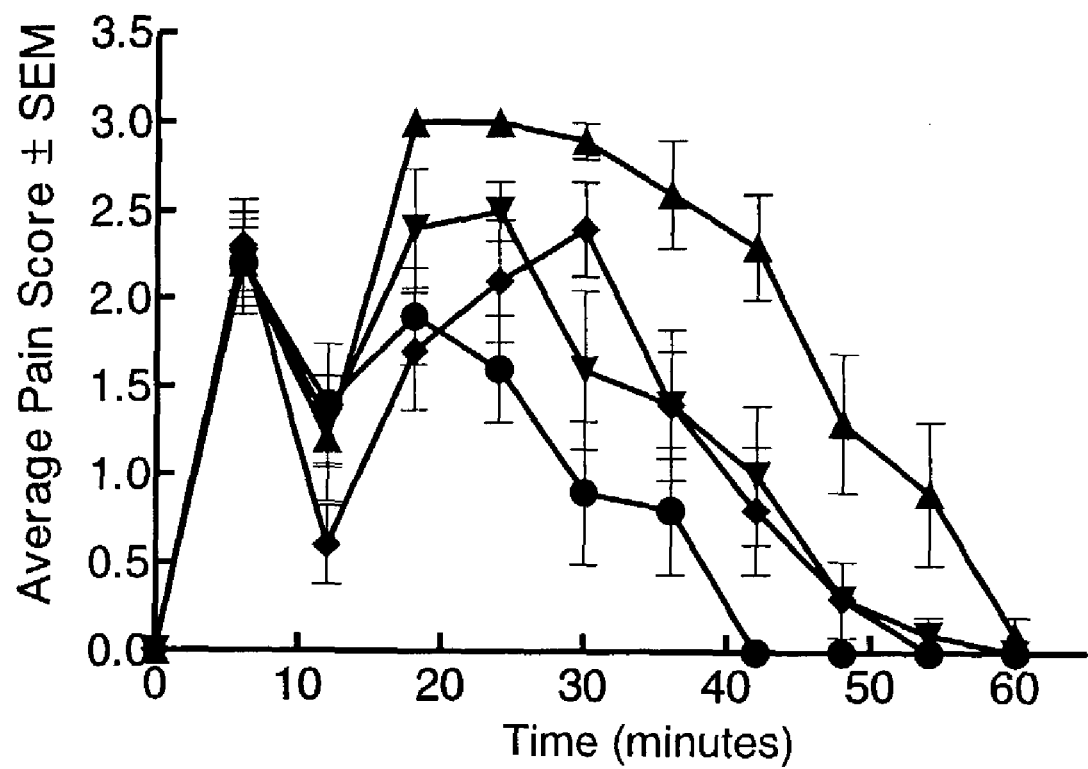

A dose response study on rats at postnatal days 7, 15, and 21 using the γPCK V5 peptide identified herein by SEQ ID NO:4. In this study, the average pain scores as a function of time were determined, as described above, using the formalin-induced pain model. The peptide was administered at dosages of 2 μM, 10 μM and 20 μM fifteen minutes after formalin injection. The results are shown in FIGS. 4A-4C for rats at postnatal day 7 (FIG. 4A), postnatal day 15 (FIG. 4B) and postnatal day 21 (FIG. 4C), where the 2 μM γPKC dose is represented by inverted triangles, the 10 μM dose of γPKC is represented by diamonds, and the 20 μM γPKC dose by circles. The control groups received 10 μM of the Tat carrier peptide and are represented by triangles.

FIGS. 4A-4C shows that inhibition of γPKC translocation attenuated phase 2 but not phase 1 of formalin-induced spontaneous pain behaviors in a dose-dependent manner. The attenuation of phase 2 behaviors was age-dependent, with the highest dose producing mild anti-nociception in 7 day old rats as compared to a more robust anti-nociception produced by all three doses in 21 day old rats. Inhibition of γPKC translocation by the peptide (SEQ ID NO:4) shortened the duration of phase 2 behaviors in both 15 day old and 21 day old rats.

Thus, in one embodiment, the invention contemplates a composition comprising a γPKC or an γPKC peptide from the V5 domain of the respective peptides for administration to a person in need of pain management, as exemplified by SEQ ID NO:3, SEQ ID NO:4, and SEQ ID NO:5. The peptides from the V5 domain of γPKC and εPKC have an analgesic activity, and effectively modulate pain.

In another embodiment, the invention-contemplates a composition comprising a combination of V5 domain peptides from the same or different PKC isozymes. The invention also contemplates a combination therapy comprised of a V5 domain PKC peptide and a non-V5 domain PKC peptide from the same or from a different isozyme. For example, a composition comprised of a γPKC V5 domain peptide, such as SEQ ID NO:4 and of an εPKC V5 domain peptide, such as SEQ ID NO:5, is prepared and administered for pain management. Compositions comprised of a γPKC V5 domain peptide and of, for example, an εPKC V1 domain peptide, such as εPKC V1-2 (SEQ ID NO:6) can also be prepared and administered.

It will be appreciated that the peptides can be used in native form or modified by conjugation to a carrier. In native form, the peptide can be formulated as needed to facilitate its transport into a cell. Suitable formulations for cell permeation are known in the art and include, for example, micelles, liposomes (charged and uncharged), and lipophilic media. When linked to a carrier, one of skill can select from a variety of peptide carriers known in the art. In addition to the Tat carrier used in the studies described above, carriers based on *Drosophila* Antennapedia homeodomain (SEQ ID NO:8; Théodore, L., et al. *J. Neurosci.* 15:7158 (1995); Johnson, J. A., et al., Circ. Res. 79:1086 (1996*b*)), where the PKC peptide is cross-linked via an N-terminal Cys-Cys bond to the Antennapedia carrier, are suitable. Polyarginine is another exemplary carrier peptide (Mitchell et al., *J. Peptide Res.*, 56:318-325 (2000); Rothbard et al., Nature Med., 6:1253-1 257 (2000)).

As noted above, FIG. 1 shows three exemplary peptides derived from the V5 domains of γPKC and εPKC. These exemplary peptides are indicated in the FIG. as SEQ ID NOS: 3, 4, and 5. It will also be appreciated that peptides homologous to these exemplary sequences and peptides having conservative amino acid substitutions, as well as fragments that retain activity, are within the scope of peptides contemplated. Exemplary modifications for SEQ ID NO:4 (RLVLAS) include the following changes shown in lower case: kLVLAS (SEQ ID NO:9); RLVLgS (SEQ ID NO:10); RLVLpS (SEQ ID NO:11); RLVLnS (SEQ ID NO:12), and any combination of the above. Other modifications include changes of one or two L to I or V, such as RiVLAS (SEQ ID NO:13); RLViAS (SEQ ID NO:14); or RiViAS (SEQ ID NO:15). Also, L and V can be changed to V, L, I, R, and/or D, as in RLiLAS (SEQ ID NO:16), RLdLAS (SEQ ID NO:17), and RidLAS (SEQ ID NO:18) or RridAS (SEQ ID NO:19). Thus, the term "a γPKC peptide derived from the V5 region of γPKC" is exemplified by the sequences identified as RLVLAS (SEQ ID NO:4) and GRSGEN (SEQ ID NO:3) and all modifications, derivations, fragments, combinations, and hybrids thereof that retain the desired activity. The term "an εPKC peptide derived from the V5 region of εPKC" is exemplified by the sequence identified as IKTKRDVN SEQ ID NO:5, and all modifications, derivations, fragments, combinations, and hybrids thereof that retain the desired activity. Thus, in all of the exemplary fragments recited above, conservative modifications and other modifications that do not appreciably alter the activity can be made and fall within the contemplated peptides.

All peptides described herein can be prepared by chemical synthesis using either automated or manual solid phase synthetic technologies, known in the art. The peptides can also be prepared recombinantly, using techniques known in the art.

III. Methods of Use

Pain is a basic clinical symptom seen by physicians and is often categorized as mild, moderate, or severe. The peptides described herein are suitable for treatment of pain in any of these categories. For example, cancer and post-operative surgical pain are often described as being in the moderate-to-severe category. Tumor infiltration of bone, nerve, soft tissue, or viscera are common causes of cancer pain. Various factors influence the prevalence of cancer pain in patients, such as the tumor type, state, and site, as well as patient variables. With respect to post-operative pain, the severity of the pain is often dependent on location and extent of intervention.

More particularly, the peptides are suited to treatment of acute or chronic pain caused, for example, by neuropathic or inflammatory conditions. Exemplary inflammatory conditions contemplated for treatment include, but are not limited to, sunburn, osteoarthritis, colitis, carditis, dermatitis, myostis, neuritis, and rheumatoid arthritis, lupus and other collagen vascular diseases, as well as post-operative surgical pain. Conditions associated with neuropathic pain include, but are not limited to, trauma, surgery, amputation, abscess, demyelinating diseases, trigeminal neuralgia, cancer, chronic alcoholism, stroke, thalamic pain syndrome, diabetes, herpes infections, and the like.

As noted above, inflammation and nerve damage can induce hyperalgesia, where a noxious stimulus is perceived as intensely painful due to a lowering of pain threshold. Accordingly, the invention contemplates a composition and a method for treating hyperalgesia in a patient. Additionally, the invention contemplates compositions and methods for treating allodynia in a subject; that is, treating the pain associated with a normally non-noxious stimulus.

The peptides are prepared for administration by combining with a pharmaceutically-acceptable carrier or diluent. Thus, a further aspect of the invention provides pharmaceutical compositions comprising a γPKC peptide or an εPKC peptide in a dosage form suitable for administration to a subject in need of pain management. Exemplary dosage forms include, but are not limited to, the peptides formulated in pharmaceutical carriers such as starch, lactose, talc, magnesium stearate, aqueous solutions, oil-water emulsions, and the like. Dosage forms suitable for injection by any route, including but not limited to intrathecal, intravenous, intraperitoneal, intramuscular, subcutaneous, can be prepared using pharmaceutical carriers such as buffered-aqueous or non-aqueous media. The peptides can be locally administered near a site of inflammation or peripheral nerve damage, by, for example, topical application, dermal or transdermal administration, or intradermal injection. Mucosal delivery is also contemplated, where the peptides are formulated for sublingual, vaginal, intranasal, or ocular delivery. It will be appreciated that certain forms of administration can achieve an initial localized site of delivery that becomes more widespread over time. For example, a buccal patch or a vaginal suppository provides an initially localized delivery at the site of application. Over time, the peptides travel in the body fluids (lymph, blood) from the site of delivery to provide a more widespread area of action. The extent of delivery can be controlled via selection of formulation and route of administration, as known to those of skill in the pharmaceutical formulation arts.

In another embodiment, administration of a peptide for pain management is preceded by determining whether a selected V5 domain peptide has specific activity for γPKC or εPCK. More particularly, a selected peptide derived from a V5 domain of γPKC or εPCK is tested in vitro or in vivo to determine if it has activity to inhibit translocation of the isozyme from which it is derived (γPKC or εPCK). In vitro and in vivo tests are described in the art (see for example, Mochly-Rosen et al., *Science*, 268:247 (1995); Mochly-Rosen et al., *FASEB*, 12:35 (1998); Mochly-Rosen et al., *PNAS USA*, 84:4660 (1987); Igwe O. J., et al., *Neuroscience* 104(3):875-890 (2001)). If the peptide is effective to inhibit translocation of its specific isozyme, it is selected for administration to a subject in need of pain management and is provided in a dosage form suitable for administration.

The amount of the peptide in the composition can be varied so that a suitable dose is obtained and an effective analgesic effect is achieved. The dosage will depend on a number of factors such as the route of administration, the duration of treatment, the size and physical condition of the patient, the potency of the peptide and the patient's response. Effective amounts of the peptide can be estimated by testing the peptide in one or more the pain models described herein.

The peptides can be administered as needed, hourly, several times per day, daily, or as often as the person experiencing the pain or that person's physician deems appropriate. The peptides can be administered prophylactically, in anticipation of pain, or can be administered as needed prior to or during an acute episode of pain. The peptides can be administered on an on-going basis for management of chronic pain, or can be administered on a short term basis prior to after an episode of pain, for example, prior to and/or after surgery.

IV. Methods of Identification

Another aspect of the invention is a method of identifying compounds that modulate pain, for example, by using the peptides described herein as research tools for identification of compounds that mimic the analgesic activity of the peptides. The invention also contemplates use of the peptides in assays to detect the site of action of the peptides or in studies on the mechanism of action of the peptides.

In identifying compounds that mimic the activity of the peptides, compounds that are able to induce analgesia, bind to cellular receptors to which the peptides bind or otherwise act in the same of a similar physiological manner as the peptides, can be identified by several techniques. For example, one method comprises adding a test compound to a biological assay known to be indicative of the activity of a γPKC peptide, such as SEQ ID NO:3 or SEQ ID NO:4. The activity of the γPKC peptide in the presence and/or absence of the test compound is determined to discern the effect of the test compound on the activity of γPKC. For example, if the biological assay in the absence of the test compound measures a certain degree of γPKC binding to a substrate or binding partner, an increase or decrease in the γPKC binding would be indicative of the test compound having agonist or antagonistic activity, respectively.

Alternatively, test compounds that modulate the activity of γPKC can be determined with an assay, followed by subsequent testing of the compound for analgesic activity. For example, a competitive binding screening assay can be used to identify compounds that mimic the activity of γPKC by adding a test compound and a detectably-labeled peptide to mammalian cells, tissue, or a receptor for the activated kinase peptide (a "RACK" or a pseudo-RACK), under conditions that allow binding of the peptide. Binding of the labeled protein to the cell, tissue, or RACK is measured. Compounds that mimic the activity of the peptide will compete for with the peptide for binding. Consequently, a smaller amount of detectable label will be measured when the test compound mimics the activity of the peptide by binding to the receptor than when the test compound does not mimic the activity of the peptide and does not bind to the receptor, or does so with less affinity.

In general, identification of compounds that mimic the activity of peptides derived from the V5 domains of γPKC and εPKC are identified by measuring the ability of a test compound to inhibit, enhance, or modulate the activity of V5 domain peptides. The activity of the V5 domain γPKC or εPKC peptides in a selected assay is measured in the presence and absence of the test compound. The assay can be a competitive binding assay, described above, or a cellular assay the monitors modulation of a second messenger production, changes in cellular metabolism, or effects on enzymatic activity. Compounds identified as mimicking or modulating the activity of the V5 domain γPKC or εPKC peptides are then tested for analgesic activity using an animal pain model, such as those described above and in the Examples.

A variety of test compounds may be screened by this method, including other peptides, macromolecules, drugs, organic compounds, chemical and/or biological mixtures, fungal extracts, bacterial extracts, and algal extracts. The compounds can be biological or synthetic in origin.

From the foregoing, it can be appreciated how various objects and features of the invention are met. Isozyme-specific peptide inhibitors of γPKC or εPKC translocation were used as therapeutic agents for pain management. The peptide inhibitors were derived from the V5 domain of γPKC and εPKC and were shown to effectively modulate the pain response in test animals. Administration of the peptides prior to a painful stimulus, during a pain episopde or during a painful stimulus, or after a painful stimulus provides an effective means to manage the pain sensation. The peptides can be administered locally at the anticipated pain site or at the pain site, or can be administered systemically via injection.

V. EXAMPLES

The following examples further illustrate the invention described herein and are in no way intended to limit the scope of the invention.

Example 1

Effect of PKCγ Peptide on Formalin-Induced Nociception

Rat pups (male and female, Sprague-Dawley) were randomly divided at selected days after birth (postnatal days 7, 15, and 21) into groups for treatments. Each group received a PKC V5-domain test peptide, a positive, comparative control peptide, a carrier peptide control, or a saline control. The V5-domain test peptide was a γPKC peptide identified herein as SEQ ID NO:4 and as the comparative control peptide was a V1 domain εPKC peptide identified herein as SEQ ID NO:6. Peptides were reversibly conjugated to a Tat-peptide carrier (SEQ ID NO:7) via a cysteine-cysteine bond at their N termini. The peptides were administered via direct lumbar puncture (intrathecal administration) at the indicated dose, typically a dose of 20 μM PKC peptide in 5 μL (7 day old pups) or 10 μL (15 and 21 day old pups) saline.

Fifteen minutes after administration of the peptides or the control substance, 1% formalin (7 day old pups) or 2.5% formalin (15 and 21 day old pups) was delivered intradermally to the paw. Spontaneous pain behaviors were recorded every two minutes for one hour following formalin injection. The time sampling method for behavioral observation was employed, in which the observer rapidly recorded the behavior of the animals every two minutes (Teng et al., *Pain,* 76:337 (1998). A score of "1" was given if the animal was licking, shaking, or elevating the hindpaw. A six minute period of observation provided a maximum pain score of "3" for each animal.

The results are shown in FIGS. 2A-2C. FIG. 2A corresponds to the study on 7 day old rat pups, where the Tat-derived-γ-PKC peptide is represented by the closed squares, the Tat-derived-εFPCK (positive control) by the open squares, the Tat carrier peptide alone by the open triangles, and saline by the open circles (n=8=10/group).

FIG. 2B corresponds to 15 day old rat pups, where Tat-derived γPCK V5 peptide is represented by the closed squares, the Tat-derived-εPCK (positive control) by the open squares, the Tat carrier peptide alone by the open triangles, and saline by the open circles (n=9-10 per test group).

FIG. 2C corresponds to the 21 day old rat pups (n=10 per test group), where the Tat-derived γPCK V5 peptide is by the closed squares, the Tat-derived-εPCK (positive control) by the open squares, the Tat carrier peptide alone by the open triangles, and saline by the open circles

Example 2

Effect of PKC V5 Peptides on Capsaicin-Induced Nociception

Adult male Sprague-Dawley rats weighing between 200-250 g were lightly anaesthetized with urethane (800 mg/kg, i.p.). The dorsal surface of each animal was painted with India ink to ensure heat was applied evenly to the dorsal surface. Baseline measurements of all animals (n=10/test group) were taken for 45 minutes for both C-fibers (0.9° C./sec heating rate) and Aδ-fibers (6.5° C./sec heating rate). The test V5 peptide was derived from the V5 region of γPKC (SEQ ID NO:4) and was conjugated to a Tat-carrier peptide (SEQ ID NO:7). As a positive comparative control, a peptide from the V1 domain of PKC (SEQ ID NO:6) was also conjugated to a Tat-carrier peptide (SEQ ID NO:7). The peptides were delivered intrathecally via direct lumbar puncture (10 μM peptide in 20 μL saline) 15 minutes prior to topical application of capsaicin to the left hind paw (100 μL of 3% capsaicin). Saline and the Tat-carrier peptide alone (SEQ ID NO:7) were also administered to two separate groups of control animals. A latency measurement was taken post peptide but prior to capsaicin application to control for direct peptide effect. Twenty minutes after the application of capsaicin, the ink was re-applied, and the dorsal surface of the hind paws was subjected to low rate heating for a maximum of 20 seconds. Foot withdrawal latencies were measured at 15 minute intervals. The results are shown in FIG. 3.

Example 3

Effect of PKC Peptides on Pre-Existing Capsaicin-Induced Nociception

Testing of V5-domain PKC peptides for treatment of pre-existing chronic pain is done as follows. The ability of the peptides to reverse established capsaicin-induced thermal hyperalgesia is determined using the procedure described in Example 2, except the test peptides are administered post-capsaicin treatment. That is, after the baseline measurements, capsaicin is administered. Twenty-five minutes later, the test substances are administered over a 10 minute period. Various concentrations of test peptides, 1 µM, 50 µM, and 100 µM are administered to the animals. Thermal testing is then done as described in Example 2.

Although the invention has been described with respect to particular embodiments, it will be apparent to those skilled in the art that various changes and modifications can be made without departing from the invention.

The invention claimed is:

1. An isolated peptide consisting of a gamma-protein kinase C (γPKC) peptide, wherein the peptide consists of between five and ten amino acid residues having at least 80% sequence identity to SEQ ID NO:4, said γPKC peptide having isozyme-specific activity for modulation of pain, and wherein the γPKC peptide is conjugated to a heterologous carrier peptide for transport across a cell membrane.

2. A peptide according to claim 1, wherein said isozyme-specific activity is an inhibitory activity that attenuates nociception.

3. The peptide according to claim 1, wherein said peptide has a sequence identified as SEQ ID NO:4.

4. A peptide according to claim 1, wherein said peptide has isozyme-specific activity for modulation of chronic pain.

5. A peptide according to claim 1, wherein said peptide has isozyme-specific activity for modulation of acute pain.

6. A peptide according to claim 1, wherein said peptide has isozyme-specific activity for modulation of pain associated with inflammation.

7. A peptide according to claim 1, wherein said peptide has isozyme-specific activity for modulation of neuropathic pain.

8. A peptide according to claim 1, wherein said peptide has isozyme-specific activity for modulation of cancer pain.

* * * * *

UNITED STATES PATENT AND TRADEMARK OFFICE
CERTIFICATE OF CORRECTION

| | | |
|---|---|---|
| PATENT NO. | : 7,459,424 B2 | Page 1 of 1 |
| APPLICATION NO. | : 10/421548 | |
| DATED | : December 2, 2008 | |
| INVENTOR(S) | : Mochly-Rosen et al. | |

It is certified that error appears in the above-identified patent and that said Letters Patent is hereby corrected as shown below:

Column 1, line 8-10 "Accordingly the United States government may have rights in this invention" should be changed to --Accordingly the United States government has rights to this invention--.

Signed and Sealed this

Tenth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,459,424 B2
APPLICATION NO.   : 10/421548
DATED             : December 2, 2008
INVENTOR(S)       : Mochly-Rosen et al.

It is certified that error appears in the above-identified patent and that said Letters Patent is hereby corrected as shown below:

On the Title Page, Item (73)
Assignee information on the title page "The Borad of Trustess of the Leland Stanford Junior University" should be changed to -- The Board of Trustees of the Leland Stanford Junior University. --

Signed and Sealed this

Ninth Day of June, 2009

JOHN DOLL
*Acting Director of the United States Patent and Trademark Office*

SEQUENCE LISTING

```
<160> NUMBER OF SEQ ID NOS: 19

<210> SEQ ID NO 1
<211> LENGTH: 65
<212> TYPE: PRT
<213> ORGANISM: Artificial Sequence
<220> FEATURE:
<223> OTHER INFORMATION: peptide from the V5 domain of gammaPKC

<400> SEQUENCE: 1

Pro Arg Pro Cys Gly Arg Ser Gly Glu Asn Phe Asp Lys Phe Phe Thr
1               5                   10                  15

Arg Ala Ala Pro Ala Leu Thr Pro Pro Asp Arg Leu Val Leu Ala Ser
            20                  25                  30

Ile Asp Gln Ala Asp Phe Gln Gly Phe Thr Tyr Val Asn Pro Asp Phe
        35                  40                  45

Val His Pro Asp Ala Arg Ser Pro Thr Ser Pro Val Pro Val Pro Val
    50                  55                  60

Met
65

<210> SEQ ID NO 2
<211> LENGTH: 51
<212> TYPE: PRT
<213> ORGANISM: Artificial Sequence
<220> FEATURE:
<223> OTHER INFORMATION: peptide from the V5 domain of epsilonPKC

<400> SEQUENCE: 2

Pro Arg Ile Lys Thr Lys Arg Asp Val Asn Asn Phe Asp Gln Asp Phe
1               5                   10                  15

Thr Arg Glu Glu Pro Val Leu Thr Leu Val Asp Glu Ala Ile Val Lys
            20                  25                  30

Gln Ile Asn Gln Glu Glu Phe Lys Gly Phe Ser Tyr Phe Gly Glu Asp
        35                  40                  45

Leu Met Pro
    50

<210> SEQ ID NO 3
<211> LENGTH: 6
<212> TYPE: PRT
<213> ORGANISM: Artificial Sequence
<220> FEATURE:
<223> OTHER INFORMATION: peptide derived from the V5 domain of the gamma
      isozyme of PKC
```

```
<400> SEQUENCE: 3

Gly Arg Ser Gly Glu Asn
 1               5

<210> SEQ ID NO 4
<211> LENGTH: 6
<212> TYPE: PRT
<213> ORGANISM: Artificial Sequence
<220> FEATURE:
<223> OTHER INFORMATION: peptide derived from the V5 domain of the gamma
      isozyme of PKC

<400> SEQUENCE: 4

Arg Leu Val Leu Ala Ser
 1               5

<210> SEQ ID NO 5
<211> LENGTH: 7
<212> TYPE: PRT
<213> ORGANISM: Artificial Sequence
<220> FEATURE:
<223> OTHER INFORMATION: peptide derived from the V5 domain of the
      epsilonisozyme of PKC

<400> SEQUENCE: 5

Ile Lys Thr Lys Arg Asp Val
 1               5

<210> SEQ ID NO 6
<211> LENGTH: 8
<212> TYPE: PRT
<213> ORGANISM: Artificial Sequence
<220> FEATURE:
<223> OTHER INFORMATION: peptide derived from the V1 domain of epsilon
      PKC

<400> SEQUENCE: 6

Glu Ala Val Ser Leu Lys Pro Thr
 1               5

<210> SEQ ID NO 7
<211> LENGTH: 10
<212> TYPE: PRT
<213> ORGANISM: Artificial Sequence
<220> FEATURE:
<223> OTHER INFORMATION: Tat-derived carrier peptide (Tat 47-57)

<400> SEQUENCE: 7

Tyr Gly Lys Lys Arg Arg Gln Arg Arg Arg
 1               5                   10

<210> SEQ ID NO 8
<211> LENGTH: 17
<212> TYPE: PRT
<213> ORGANISM: Artificial Sequence
<220> FEATURE:
<223> OTHER INFORMATION: Drosophila Antennapedia homeodomain-derived
      carrier peptide

<400> SEQUENCE: 8

Cys Arg Gln Ile Lys Ile Trp Phe Gln Asn Arg Arg Met Lys Trp Lys
 1               5                   10                  15

Lys
```

```
<210> SEQ ID NO 9
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 9

Lys Leu Val Leu Ala Ser
 1               5

<210> SEQ ID NO 10
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 10

Arg Leu Val Leu Gly Ser
 1               5

<210> SEQ ID NO 11
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 11

Arg Leu Val Leu Pro Ser
 1               5

<210> SEQ ID NO 12
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 12

Arg Leu Val Leu Asn Ser
 1               5

<210> SEQ ID NO 13
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 13

Arg Ile Val Leu Ala Ser
 1               5

<210> SEQ ID NO 14
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC
```

```
<400> SEQUENCE: 14

Arg Leu Val Ile Ala Ser
 1               5

<210> SEQ ID NO 15
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 15

Arg Ile Val Ile Ala Ser
 1               5

<210> SEQ ID NO 16
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 16

Arg Leu Ile Leu Ala Ser
 1               5

<210> SEQ ID NO 17
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 17

Arg Leu Asp Leu Ala Ser
 1               5

<210> SEQ ID NO 18
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 18

Arg Ile Asp Leu Ala Ser
 1               5

<210> SEQ ID NO 19
<211> LENGTH: 6
<212> TYPE: PRT
<213> ORGANISM: Artificial Sequence
<220> FEATURE:
<223> OTHER INFORMATION: modificiation of a peptide derived from the V5
      domain of the gamma isozyme of PKC

<400> SEQUENCE: 19

Arg Arg Ile Asp Ala Ser
 1               5
```